United States Patent [19]

Memmert et al.

[11] Patent Number: 4,927,751

[45] Date of Patent: May 22, 1990

[54] PROCESSES FOR OBTAINING EXOENZYMES BY CULTURE

[75] Inventors: Klaus Memmert; Christian Wandrey, both of Jülich, Fed. Rep. of Germany

[73] Assignee: Kernforschungsanlage Juelich Gesellschaft mit beschraenkter Hagtung, Juelich, Fed. Rep. of Germany

[21] Appl. No.: 882,349

[22] Filed: Jul. 7, 1986

[30] Foreign Application Priority Data

Jul. 6, 1985 [DE] Fed. Rep. of Germany ....... 3524273
Apr. 19, 1986 [DE] Fed. Rep. of Germany ....... 3613311

[51] Int. Cl.⁵ .............. C12Q 3/00; C12N 9/00; C12N 9/28; C12N 9/56
[52] U.S. Cl. ..................... 435/3; 435/183; 435/202; 435/222; 435/813; 435/818
[58] Field of Search ............ 435/813, 807, 818, 3, 435/183, 202, 221, 222

[56] References Cited

U.S. PATENT DOCUMENTS

| | | | |
|---|---|---|---|
| 4,042,460 | 8/1977 | Diers | 435/801 X |
| 4,167,450 | 9/1979 | Chesbro et al. | 435/3 |
| 4,306,026 | 12/1981 | Maslen et al. | 435/813 X |
| 4,424,559 | 1/1984 | Lorinz et al. | 435/3 X |
| 4,452,889 | 6/1984 | Sonoi | 435/813 X |
| 4,680,267 | 7/1987 | Eppstein et al. | 435/807 X |

FOREIGN PATENT DOCUMENTS 219036 2/1985 Fed. Rep. of Germany .......... 435/3

OTHER PUBLICATIONS

Wang et al Fermentation and Enzyme Technology John Wiley & Sons NY (1979) pp. 98–100.
Kjaergaard, Biotechnology Letters, "Influence of Succinic Acid on the Extracellular α-amylase Production by Chemostat-grown *Bacillus Licheniformis*", pp. 93–96, (1979).
Gandhi et al "Effect of Carbon Dioxide on the Formation of α-Amylase by *Bacillus subtilis* Growing in Cont. Batch Cultures", Biotechnol. and Bioeng. 1975, 17.
Fujio et al "Isoamylase Production by Aerobacter aerogenes" J. Ferment. Technol. vol. 50, No. 8, pp. 553, 1972.
Davis "The production of amylase by *Bacillus stearothermophilus* in continuous culture" J. Appl. Chem. Biotech. Band 26, 1976 Chemical Abstracts, vol. 89, 1978 No. 193652h Wiersma et al.
Bacteriol. Rev. 41 (3): (1977) Priest "Extracellular Enzyme Synthesis in the Genus Bacillus".

Primary Examiner—Thomas G. Wiseman
Assistant Examiner—Anne Brown
Attorney, Agent, or Firm—Foley & Lardner, Schwartz, Jeffery, Schwaab, Mack, Blumenthal & Evans

[57] ABSTRACT

Exoenzymes, such as proteases, xylanases and amylases, are obtained continuously by cultivation of exoenzyme-producing microorganisms in one step in a fermenter which is operated with continuous flow and in which a deficiency state corresponding to maximal enzyme productivity is effected. Optical density of the culture (as a measure of the biomass density) and exoenzyme concentration in culture can be monitored to control the timing and extent of the deficiency state. It is particularly advantageous to impose an oxygen limitation and to maintain the deficiency state continuously by exerting an effect on the oxygen input.

41 Claims, 5 Drawing Sheets

PROCESSES FOR OBTAINING EXOENZYMES BY CULTURE

BACKGROUND OF THE INVENTION

The present invention relates to processes for continuously obtaining extracellular or secreted enzymes (exoenzymes) by cultivation of exoenzyme-producing bacteria in a continuous-flow fermenter.

Exoenzymes such as proteases, xylanases and amylases are obtained by cultivation of bacteria, in particular of strains of the genus Bacillus. To date, exoenzymes have been prepared only by discontinuous (batch) fermentation, because the secretion of these enzymes by the microorganisms rapidly diminishes in continuous culture (chemostat). See, generally, Priest, "Extracellular Enzyme Synthesis in the Genus Bacillus," *Bacteriol. Rev.* 41 (3): (1977), the contents of which are hereby incorporated by reference.

The reasons for the diminution in exoenzyme secretion as soon as a batch fermentation is converted into a continuous fermentation have not yet been completely elucidated. The observation that exoenzyme production in batch cultures takes place mainly in the late logarithmic and stationary phases and before sporulation, and not, in contrast, in the logarithmic phase of growth (Dancer and Mandelstam, "Criteria for Categorizing Early Biochemical Events Occurring During Sporulation of *B. Subtilis,*" *J. Bacteriol.*: 411–415 (1975)), leads to the conclusion that the formation of exoenzymes, while generally constitutive, is subject to catabolite repression (Schaeffer, "Sporulation and the Production of Antibiotics, Exoenzymes, and Exotoxins," *Bacteriol. Rev.*: 48–71 (1969)). Catabolite repression is also suggested by the observation that the production of exoenzymes increases with the difficulty of utilization by the organisms of the carbon source in the medium (Moses and Sharp, "Intermediary Metabolite Levels in *Escherichia coli,*" *J. Gen. Microbiol.* 71: 181–190)), e.g., the yield of enzyme is better when glycerol or lactose, rather than glucose is used as the carbon source.

In light of catabolite repression of this nature, there have been various proposals of multistage, continuous fermentation processes. See Tsaplina & Loginova, "Production of bacterial proteinase during continuous cultivation," in 5th INT. FERMENTATION SYMP. VERSUCHS-UND LEHRANSTALT FUR SPIRITUSFABRIKATION UND FERMENTATIONSTECHNOLOGIE 262 (H. Dellweg ed., Berlin). But these proposed processes have proved unsatisfactory for industrial production.

SUMMARY OF THE INVENTION

It is therefore an object of the present invention to provide a process for cultivating exoenzyme-producing microorganisms so as to obtain enhanced production of exoenzymes in culture.

It is also an object of the present invention to provide a process for producing exoenzymes by continuous fermentation.

These objects are achieved, in accordance with the present invention, by carrying out fermentation with an exoenzyme-producing microorganism in one step, during which (a) continuous limitation of growth appropriate for maximal exoenzyme productivity is effected or (b) repeated or periodic reductions are brought about in the concentration of culture biomass by at least 30% by inhibition of growth.

More specifically, there has been provided, in accordance with one aspect of the present invention, a process for obtaining exoenzymes by continuous-flow fermentation, which comprises cultivating an exoenzyme-producing microorganism in one step in a fermenter under conditions such that multiplication of the microorganism in culture declines during at least part of the growth-phase of the culture, whereby production of an exoenzyme by the microorganism is enhanced during a transient state of restricted multiplication after growth inhibition. In a preferred embodiment, multiplication of the exoenzyme-producing microorganism is actively inhibited repeatedly, over at least two periods, such that the culture undergoes a reduction in biomass concentration of at least 30% during each period and passing said transient state while increasing again. In another preferred embodiment, multiplication of the microorganism is subject to continuous limitation caused by continuously holding said transient state.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention is further described below by reference to the drawings, which are graphs plotting the variation over time of FIG. 1: continuous xylanase formation according to the present invention.

DETAILED DESCRIPTION OF THE PREFERRED EMBODIMENTS

Figure 1:
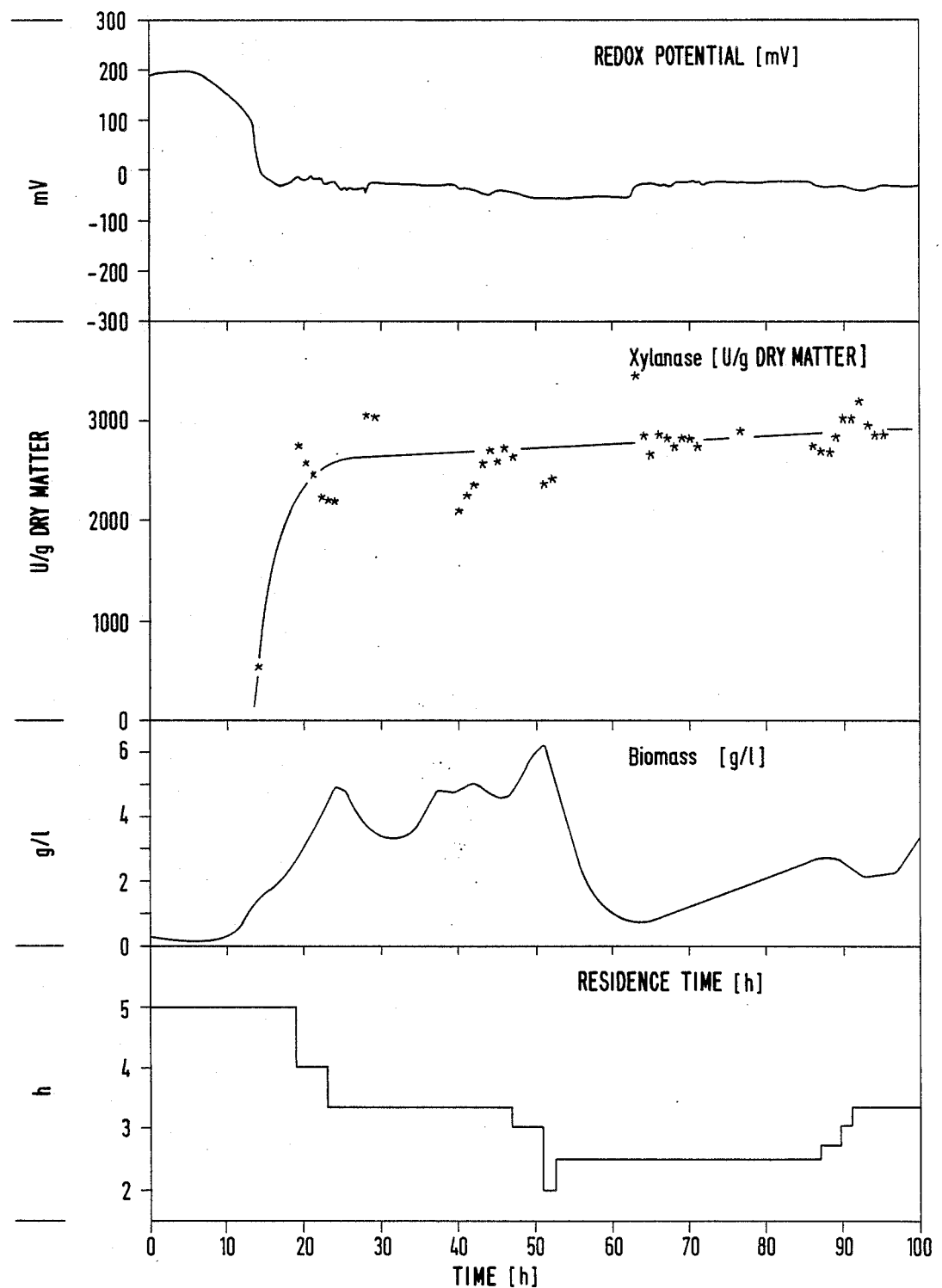

It has been discovered that, surprisingly, the production of exoenzymes, which in conventional processes substantially ceases when a steady state of fermentation is attained, can be maintained or restimulated if the culture is exposed to a particular deficiency state. As explained in greater detail below, a state of this type can be (1) continuously adjusted by a control system that responds sensitively to transition states of the culture or (2) achieved intermittently by repeatedly effecting in the culture a state of multiplication following a reduction characterized by changes in concentration of the biomass of at least 30%.

It has also been discovered that a repeated, in particular periodic, alternation of reduction and multiplication phases of this type will arise spontaneously in the culture if at least one of the conditions necessary for growth is cut back to a point where periodic increases and decreases in the biomass ("biomass pulsations") take place. For purposes of this description, these spontaneous alternations in the biomass of a culture will be called the "characteristic oscillations" of that culture. The phenomenon of characteristic oscillations can be exploited, in accordance with the present invention, by adjusting a culture parameter crucial to growth, such as pH level, to a value near an extreme in the range of values acceptable to the cultured microorganism, thereby inducing biomass pulsations as described above. The resulting oscillations in biomass density are associated, in turn, with enhanced (repeatedly induced) exoenzyme production, as explained in greater detail below.

It is particularly advantageous, however, to initiate the repeated reduction by a repeated imposition, for relatively short periods, of a growth-inhibiting effect brought about, for example, by shifting the pH or the temperature out of the range which is tolerated by the cultured microorganism, or by cutting back on necessary nutrients and the like. The duration of this growth-inhibiting effect should be such as to bring about the desired reduction in biomass, where appropriate, after a time lag. For the purposes of this description, a single alteration of biomass increase and subsequent decrease will be called a "period," whether the alteration is part of a characteristic oscillation or is actively induced by imposition of a growth-inhibiting effect (with constant or variable period as convenient).

The timing and nature of the inhibitory conditions to be applied depend on the culture conditions and, in particular, on flow rates (D) and/or residence times ($\tau$) respectively, where "residence time" is the inverse of flow rate and refers to the interval during which a unit volume of culture virtually (statistically) remains in the reactor. It is particularly advantageous for the period to last 1 to 10, in particular 6 to 8, residence times, and for the growth-inhibiting effect to have a duration, respectively, of 0.01 to 5, particularly 0.1 to 1, and specifically for about 0.5, residence times. Advantageous flow rates, in turn, are in the range 0.01 to 2 $h^{-1}$, in particular 0.05 to 1 $h^{-1}$, and specifically 0.1 to 0.5 $h^{-1}$.

For continuous production it is possible simply to monitor continuously the optical density of the culture, since optical density corresponds to the biomass density, and to use it for control purposes. In this way, an approach close to the steady-state (when change in biomass density per residence time varies by 20% or less) can be detected in good time and used on each occasion to trigger the growth-inhibiting effect. Because of the resulting "stress conditions," there occurs during each period a large decrease in the biomass density, which can extend beyond the duration of the stress phase, followed by a recovery and renewed steep increase in the production of exoenzymes.

It is also possible to monitor exoenzyme concentration for fine control. Thus, a decrease in the exoenzyme concentration at any particular time less than about ½ of the maximum concentration prior to that time is used as a signal for triggering the growth-inhibiting effect, which is maintained until the biomass density has fallen to less than about ⅔ of its steady-state value.

Detailed investigation of the individual periods have shown, surprisingly, that the production of the enzyme does not start until the level of available oxygen has decreased to a particular value. This phenomenon can be detected only by sensitive measurement of redox potential in culture, but there nevertheless is a close correlation between enzyme productivity and oxygen availability.

It is therefore possible to attain virtually continuous enzyme production if a decreased level of available oxygen corresponding to maximal exoenzyme production is maintained continuously in the culture. For this purpose, the redox potential in the fermenter, a very sensitive indicator of the oxygen content of the culture, is monitored and used as a control parameter for oxygen input, which can be varied, in particular, by the stirring speed. Stirring speeds ranging up to about 1,000 rpm with aeration at 0.3 to 3 unit volumes of air per unit volume of medium per minute ("VVm"), in particular 1 to 2 VVm, are preferred.

It is beneficial for the culture to contain a known antifoaming agent, for example, polypropylene glycol or silicone oil, to suppress, where appropriate, pronounced foam formation during the oxygen input controlled by the stirring speed.

The redox potential corresponding to maximal exoenzyme production depends on the parameters selected for the fermentation, such as the pH, the composition and concentration of nutrients, the aeration rate, the microorganism selected for culturing, and the temperature. Thus, the oxygen input which is to be adjusted in each instance (or the redox potential which is to be maintained in each instance) is most expediently determined right at the outset for a specific production in the particular fermentation system.

The control of oxygen input as a function of redox potential, according to the present invention, means that the bacterial culture is prevented from reaching a steady state, that is, the culture shows a continuous tendency for its concentration to increase or, alternatively, to "wash out" when loss of biomass in the fermenter due to flow-through outstrips the increase of biomass due to growth. It is therefore very beneficial for the present invention for biomass concentration to be kept within the specific limits. Wash-out can be counteracted, for instance, by reducing flow-through, by enhancing growth, or by retaining biomass in the fermenter, e.g., by immobilization of the cultured microorganism or by filtration or centrifugation of the culture medium.

For this purpose, a second control system can be provided that continuously monitors the biomass concentration in the fermenter (for example, via optical density) and controls it by variation of residence time in the fermenter and/or of oxygen availability, as indicated by the via the redox potential of the culture. In any event, the redox potential should remain in the range for optimal enzyme production.

During oxygen-limited exoenzyme formation in a continuous-flow fermenter, according to the present invention, it is preferable for biomass concentration in the reactor to be maintained as high as possible without being subject to any nutrient limitation (carbon, nitrogen, etc.). As previously indicated, it is also possible for the biomass to be retained in the fermenter by known procedures (immobilization, filtration, centrifugation, etc.), and for an optimal biomass concentration to be maintained by varying the proportion kept in the fermenter.

The microorganisms suitable for use in the present invention are exoenzyme-producing bacteria, particularly bacteria of the genus Bacillus. For example, bacteria of the species *Bacillus amyloliquefaciens*, as represented by deposited strains DSM 7 and DSM 1061, can be used to advantage in practicing the present invention. The temperature for culturing exoenzyme-producing bacteria in accordance with the present invention is conveniently in the range from about 30° to 37° C.

In each of the following examples, bacteria of the strain *Bacillus amyloliquefaciens* DSM 7 were cultivated in a stirred vessel reactor (fermenter) under the following conditions:

| | |
|---|---|
| 7-liter fermenter | (Type BIOSTAT"E" supplied by B. BRAUN, Melsungen) |
| Operating Volume | 4 liters (Examples 1–3) or 3 liters (Examples 4–5) |
| Temperature | 37° |
| Aeration | 6 l/min compressed air [1.5 VVm (Examples 1–3) or 2 VVm (Examples 4–5)] |
| Stirrer type | Flat-blade turbo stirrer |
| Speed | Examples 1–3: 0 rpm (adequate mixing achieved by air in-flow) Examples 4 and 5: 300 rmp (if not altered by the the control system) |

The culture medium, which was sterilized beforehand, had the following composition:

| | |
|---|---|
| 20 g | glycerol |
| 6 g | $(NH_4)_2SO_4$ |
| 1.67 g | $NaNo_3$ |
| 0.52 g | $Mg(NO_3)_2.7H_2O$ |
| 1 g | yeast extract |
| 2.72 g | $KH_2PO_4$ |
| 0.5 g | citric acid |
| 72 mg | $CaCl_2.2H_2O$ |
| 10 mg | $FeSO_4.7H_2O$ |
| 5 mg | $MnSO_4.H_2O$ |
| $H_2O$ to 1,000 ml | |

For Examples 4 and 5 (with the stirrer operating), the medium additionally contained in 1 liter
0.083 ml polypropylene glycol 2000 and
0.083 ml silicone antifoam emulsion M 30 (supplied by Serva).

COMPARISON EXAMPLE

The fermenter was inoculated at time $t=0$ h with 200 ml of a preculture of *B. amyloliquefaciens* DSM 7 which had been cultured in a shaken flask, and was first operated as a batch culture (discontinuously) for 16 hours.

From $t=16$ h the fermentation was carried out continuously, with a constant volumetric flow of fresh medium pumped into the fermenter and the same amount of fermenter contents continuously drained off. The constant volumetric flow as 220 ml/h ($D=0.055$ $h^{-1}$, $\tau=18.2$ h). The pH was controlled at a constant pH 6.0.

Figure 2:
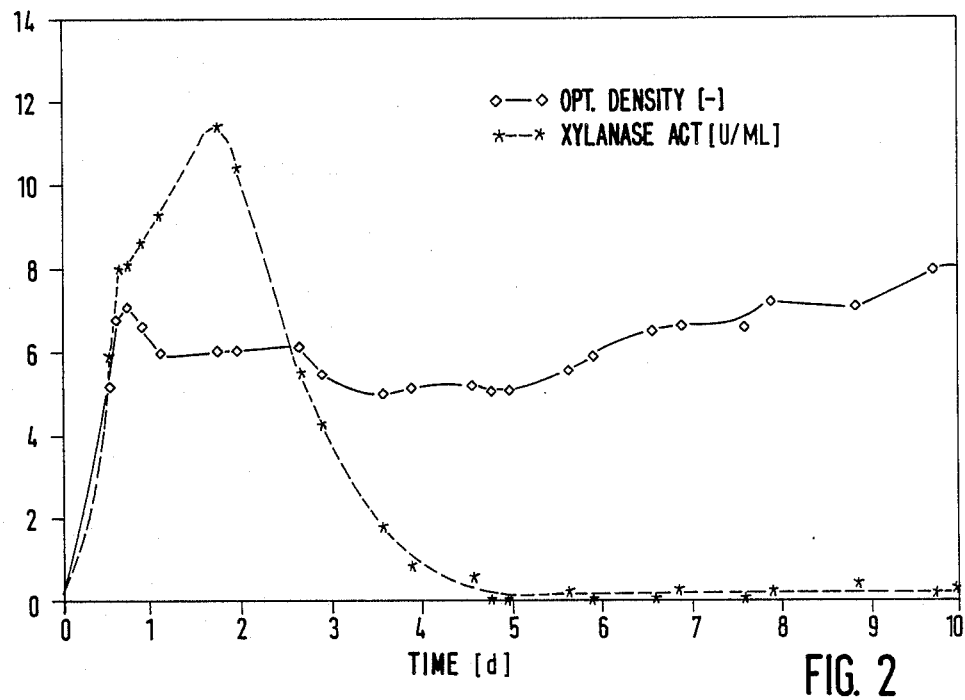
FIG. 2: uncontrolled xylanase formation of a conventional nature in a continuous-flow fermenter.

These conditions were kept constant for 13 residence times. During this period, the biomass concentration remained approximately constant (steady state), while the xylanase concentration decreased from 11 U/ml to below 0.5 U/ml (see FIG. 2).

EXAMPLE 1

After inoculation, the fermentation was carried out under the same conditions as described in the comparison example, first discontinuously for 15 hours and then continuously at 375 ml/h ($D=0.094$ $h^{-1}$; $\tau=10.7$ h). The pH was kept constant at pH 5.5 for the first 336 hours and thereafter kept constant at pH 5.1.

Figure 3:
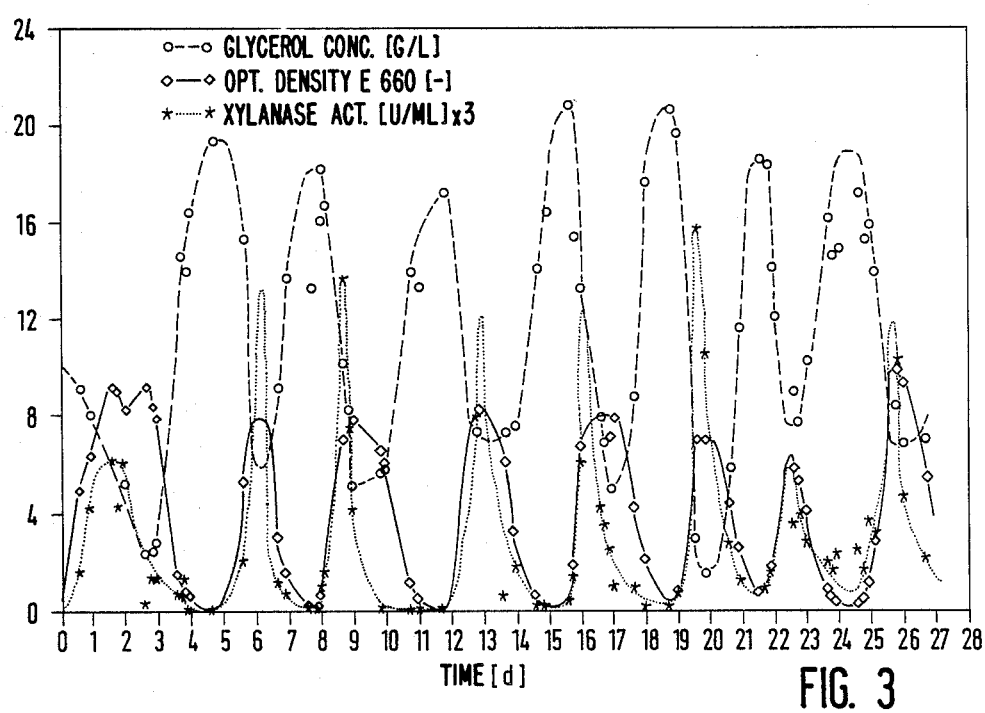
FIG. 3: optical density, xylanase concentration and glycerol concentration during continuous fermentation with spontaneous biomass pulsation.

During continuous operation, pronounced biomass pulsations arose spontaneously at both pH values (see FIG. 3, optical density). The pulsations were characterized in particular by a steep, renewed rise in the biomass during each period. Throughout the duration of the test it was observed that xylanase production resumed during the renewed increase in the biomass. The pattern of variation in glycerol concentration was essentially 180° out of phase with the observed variation in the optical density.

EXAMPLE 2

Figure 4:
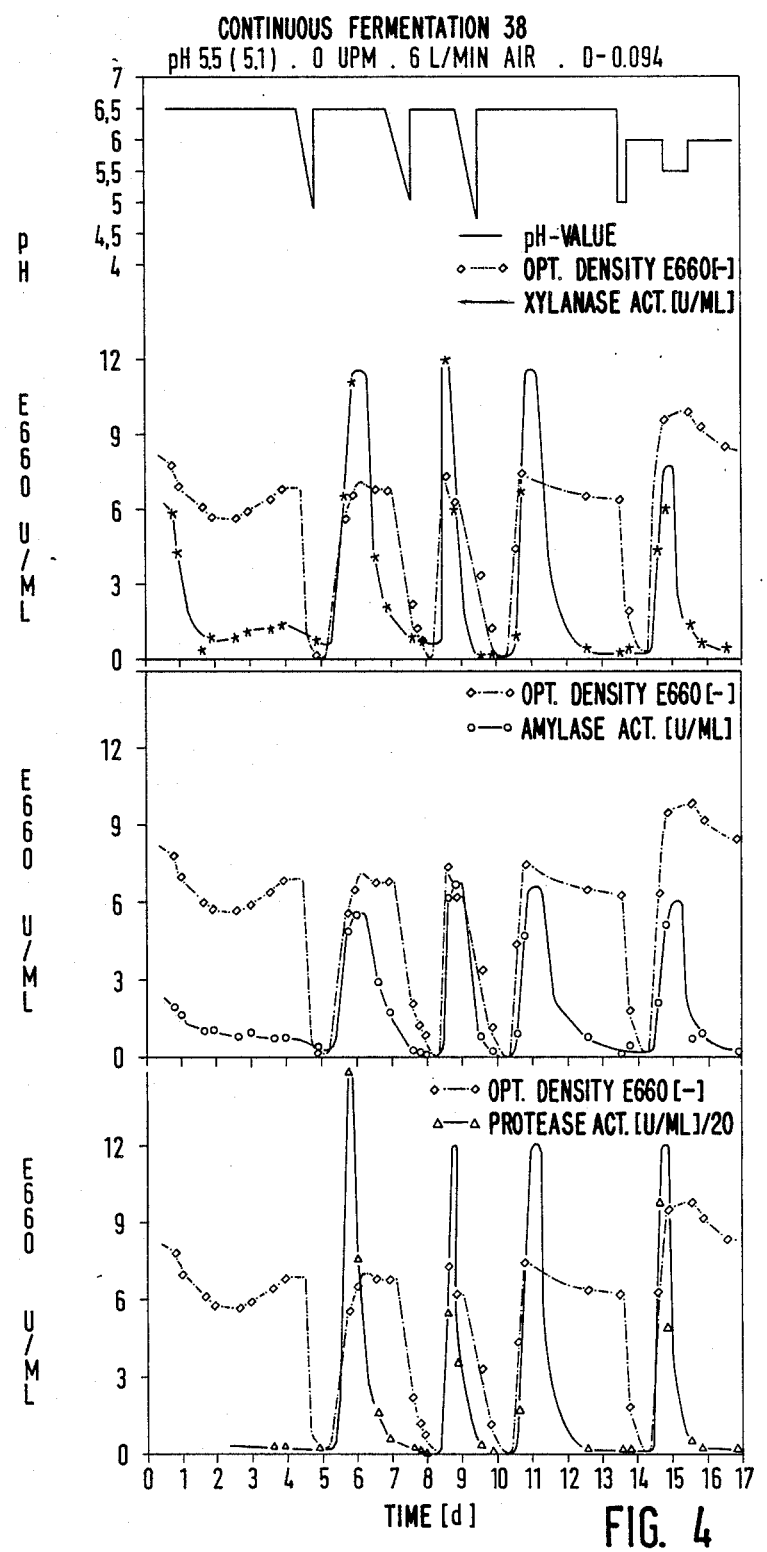
FIG. 4: optical density, exoenzyme concentration and pH during continuous fermentation (with repeated short-term growth inhibition) for xylanase, amylase and protease.

After inoculation, the fermentation was carried out under the same conditions as described in the comparison example, continuously from the outset ($t=0$ h) at 400 ml/h ($D=0.1$ $h^{-1}$; $\tau=10$ h). The pH was initially maintained constant at pH 6.5. After the biomass concentration had settled into a steady state and the exoenzyme concentration had decreased, the pH control system was switched off at time $t=107$ h for 1 residence time (10 h). This resulted in the pH falling of its own accord to pH 5.0. At time $t=117$ h, the pH control system was switched on again, and this resulted in immediate correction of the pH back to pH 6.5. During the period when the pH had shifted outside the range tolerated by the bacterium (pH 6 to 8), a large reduction in biomass concentration was observed and, thereafter, a steep renewed increase in the biomass concentration. The latter was accompanied by a marked increase in the exoenzyme concentration (see FIG. 4 for xylanase, protease and amylase).

After the biomass had again settled into a steady state and the exoenzyme concentrations had again subsided, at time $t=168$ h the pH control system was again switched off for 1.5 residence times (15 h).

The pH decreased without intervention to pH 5.0, and from $t=183$ h was returned to a constant pH of 6.5 by switching on the pH control system again.

Once more, a renewed decrease in the biomass concentration was observed, followed by a steep increase in the biomass concentration, which was again accompanied by a marked increase in exoenzyme concentrations.

In a corresponding manner, the pH control system was switched off for 14 hours between $t=215$ h and $t=229$ h, resulting in a drop in pH to 4.7. The behavior of the biomass concentration and the exoenzyme concentrations, respectively, was analogous to what occurred during the first two shifts in pH.

At time $t=325$ h the pH was actively reduced to pH 5.0 by addition of acid by the pH control system, and the pH was maintained constant at 5.0 for 0.6 residence times (6 hours). The pH was raised thereafter to 6.0 by the pH control system, and was maintained constant at that value. The behavior of the biomass concentrations and the exoenzyme concentration during this procedure was again the same as during the spontaneous pH decrease.

EXAMPLE 3

After inoculation, the fermentation was carried out as described in the comparison example, continuously from time t=0.5 h at 370 ml/h (D=0.093 h$^{-1}$, τ=10.8 h).

Figure 5:
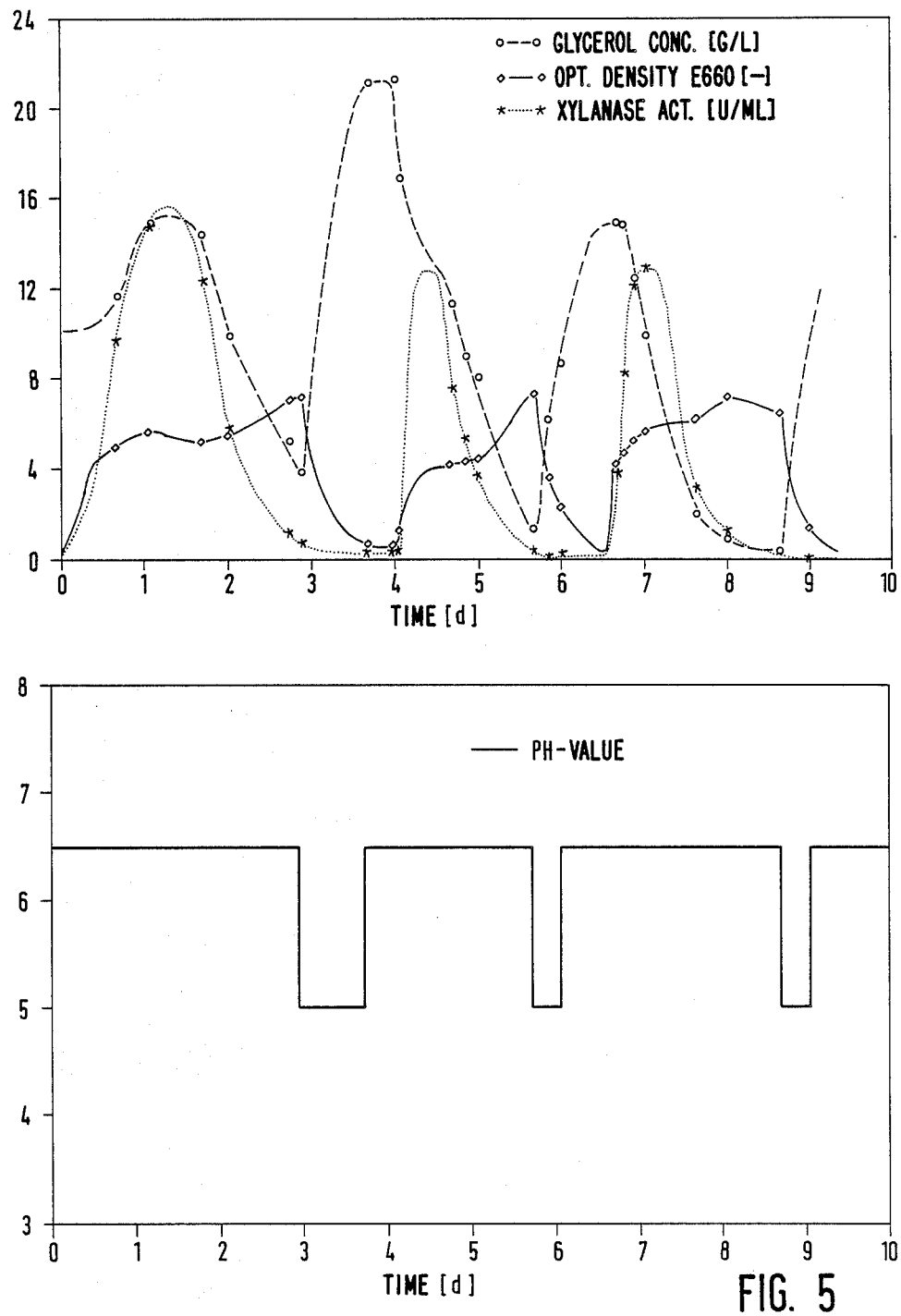
FIG. 5: optical density, xylanase concentration, glycerol concentration and pH during continuous fermentation, with repeated short-term growth inhibition according to the present invention.

The pH was actively reduced from a constant 6.5 to a constant 5.0 for 17 hours (1.6 residence times) from t=69 h onward, and for 8 hours each (0.75 residence times) from t=136 h and t=208 h onward, by means of the pH control system. The behavior of the biomass concentration and the xylanase concentration corresponded to the observations described in Example 2 (see FIG. 5.)

Other tests indicate that this procedure also works when other carbon sources than glycerol are used, for example, lactose and starch.

The species *Bacillus subtilis*, which is related to *Bacillus amyloliquefaciens*, showed a similar response to the growth-inhibition regimen of the present invention.

Although the growth-inhibiting effect chosen for biomass reduction in each of the above examples was a reduction in pH, which can be brought about in a very straightforward manner, other methods of inhibition, such as increasing pH or shifting temperature, are effective in the same way.

EXAMPLE 4

Figure 6:
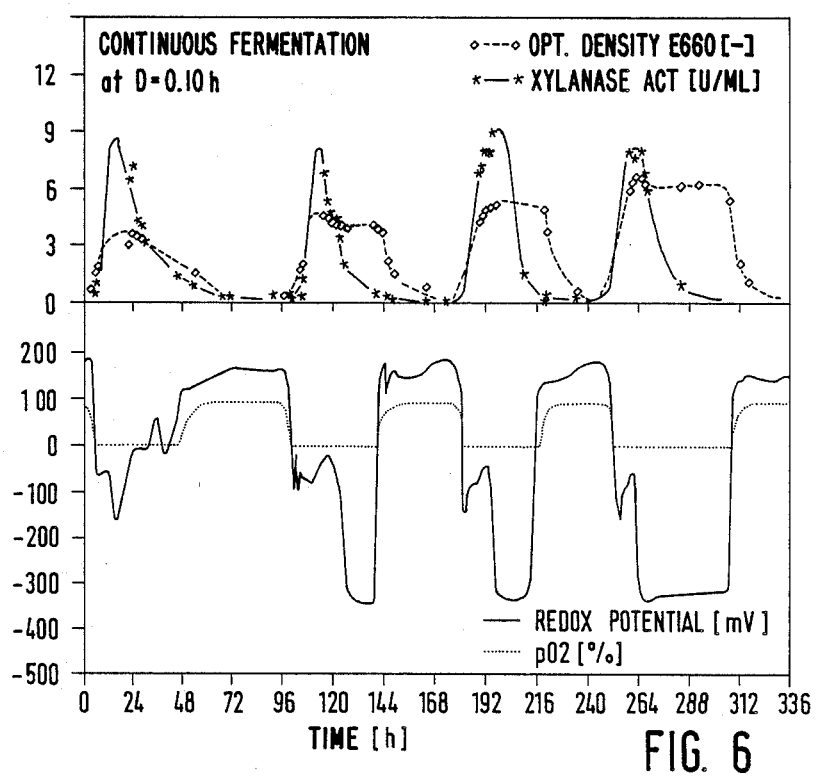
FIG. 6: quasi-continuous xylanase formation with repeated decreases in the pH, the graph of redox potential also being shown.

FIG. 6 shows the change in redox potential, in a continuous-flow fermenter, during xylanase formation that was initiated periodically by repeated pH reduction as described above. It is apparent that maximal enzyme concentrations in the culture coincide with moderate redox potentials in the decreasing regions of the redox curves, which redox potentials were around −50 mV in the present xylanase formation at pH 6 and a residence time of 5 hours.

EXAMPLE 5

The redox control shown in this example was brought about by use of a PID controller (supplied by Foxboro) which stabilizes the redox potential at a predetermined value by controlling the speed of rotation of the fermenter stirrer dependent on the monitored redox potential value.

The bacterial culture in the fermentation, which ran continuously for a prolonged period, was forced to a reduction in the biomass density by a decrease in the pH at time t=1960 h to 1964 h, and it started to increase substantially again from about t=1977 h onward (FIG. 1; plot C; the abscissa starts at t=1970 h).

At the same time the biomass increased, there was a large decrease in the redox potential up to about t=1985 h, and it then stayed in the region of about 0 to −50 mV (plot A). The redox control system was switched on, at time t=1988 h, before the redox potential could decline further, as is evident from FIG. 6. Whereas the speed of rotation of the fermenter stirrer had been constant at 300 rpm up to this time, the stirrer rotation speed was externally altered by the redox control system from t=1988 h in order to keep the redox potential at the preset redox target level in each case.

The first redox target level was selected at −15 mV from t=1988 to 1992 h. Since this target was slightly above the final uncontrolled redox figure, it was possible for the biomass concentration initially to increase further. In order to prevent an excessive increase or decrease in the biomass, the residence time of the continuous culture was varied at t=1989 h and at subsequent times (plot D). Primarily to likewise influence the biomass density, the redox target level was varied within the range from −15 to −50 mV.

Throughout the period when the redox was controlled, the enzyme concentration changed approximately in parallel with the biomass density, so that the enzyme yield stayed constant in the range from 2000 to 3000 U of xylanase per g of dry biomass (plot B).

The example described above relates to the formation of xylanase. Similar results were obtained for protease and amylase.

The end-product solution from the fermenter is worked up by known methods, for example, by centrifugation or crossflow filtration, with continuous removal of the biomass from the liquid phase. The enzyme or enzymes produced by the cultured microorganism can then be removed from the liquid phase, again via a conventional technique, such as by salting out, and thereafter isolated or purified.

What is claimed is:

1. A process for obtaining exoenzymes by continuous-flow fermentation, comprising the steps of
    (A) providing a culture of an exoenzyme-producing microorganism in one fermenter which provides an output solution;
    (B) imposing on said culture in said fermenter a continuous modification of growth conditions under non chemastatic conditions, wherein said continuous modification is predetermined to effect a restricted multiplication of said microorganism, such that a maximum exoenzyme production by said culture is repeatedly obtained;
    (C) continuing said modification of growth conditions to maximize exoenzyme production; and then
    (D) recovering exoenzyme from said output solution from said fermenter.

2. A process as claimed in claim 1, wherein restricted multiplication of said microorganism is effected by shifting the pH of said culture to a value outside a range tolerated by said microorganism.

3. A process as claimed in claim 1, wherein restricted multiplication of said microorganism is effected by shifting the temperature of said culture to a value outside a range tolerated by said microorganism.

4. A process as claimed in claim 1, wherein restricted multiplication of said microorganism is effected by adjusting the availability of a nutrient necessary to said microorganism.

5. A process as claimed in claim 1, wherein said conditions in said fermenter are such that multiplication of said microorganism undergoes spontaneous oscillations, whereby biomass in said fermenter periodically increases and decreases.

6. A process as claimed in claim 1, wherein restricted multiplication of said microorganism is effected by decreasing the availability of oxygen to said culture.

7. A process as claimed in claim 6, wherein said availability of oxygen is continuously limited.

8. A process as claimed in claim 7, further comprising the monitoring of the redox potential of said culture as an indicium of oxygen availability.

9. A process as claimed in claim 8, wherein said redox potential is maintained at between about 0 and −100 mV, said culture having a pH around 6.0.

10. A process as claimed in claim 9, wherein said redox potential is maintained between about −15 and −50 mV.

11. A process as claimed in claim 1, wherein said culture has a biomass concentration that is maintained at the highest level possible without subjecting said culture to a nutrient limitation.

12. A process as claimed in claim 11, wherein said biomass concentration is maintained within predetermined limits by varying oxygen availability to said culture or residence time in said fermenter.

13. A process as claimed in claim 12, wherein a predetermined proportion of biomass comprised of said culture is retained in said reactor.

14. A process as claimed in claim 1, wherein said exoenzyme-producing microorganism is a bacterium of the genus Bacillus.

15. A process as claimed in claim 14, wherein said bacterium of the genus Bacillus selected from the group consisting of *Bacillus amyloliquefaciens* and *Bacillus subtilis*.

16. A process as claimed in claim 15, wherein said *B. amyloliquefaciens* is DSM 7 or DSM 1061.

17. A process as claimed in claim 1, wherein said fermenter has flow rates ranging from about 0.01 to 2 $h^{-1}$.

18. A process as claimed in claim 17, wherein said fermenter has flow rates ranging from about 0.05 to 1 $h^{-1}$.

19. A process as claimed in claim 18, wherein said fermenter has flow rates ranging from about 0.1 to 0.5 $h^{-1}$.

20. A process as claimed in claim 1, wherein said fermenter comprises a stirred vessel reactor having a temperature of about 30° to 37°, aeration at about 0.3 to 3 VVm and a pH between about 6 to 8, said reactor being stirred at up to 1,000 rpm.

21. A process as claimed in claim 20, wherein said culture is cultivated using a nutrient medium that contains at least one carbon course selected from lactose, starch and glycerol.

22. A process as claimed in claim 1, wherein said exoenzyme is one from a group consisting of amylase, xylanase and protease.

23. A process as claimed in claim 1, wherein a predetermined proportion of biomass comprised of said culture is retained in said reactor.

24. A process for obtaining exoenzymes by continuous-flow fermentation performed in only one fermenter, comprising the steps of
  (A) providing a culture of an exoenzyme-producing microorganism in one fermenter which provides an output solution;
  (B) imposing on said culture a transient modification of growth conditions in said fermenter, wherein said modification effects a restricted multiplication of said microorganism, such that a maximum exoenzyme production by said culture is repeatedly obtained, and wherein (1) said modification of growth conditions is imposed each time the exoenzyme concentration in said culture decreases to less than 50% of a preceding maximum value and (2) said restricted multiplication results in a biomass decrease, in said culture, of more than 30%;
  (C) repeating said modification of growth conditions to achieve said maximum exoenzyme production; and then
  (D) recovering exoenzyme from said output solution from said fermenter.

25. A process as claimed in claim 24, wherein multiplication of said organism is inhibited during each period for an interval of between about 0.01 and 5 residence times in length.

26. A process as claimed in claim 25, wherein said interval is between about 0.1 and 1 residence times in length.

27. A process as claimed in claim 26, wherein said interval is about 0.5 residence times in length.

28. A process as claimed in claim 25, wherein each period is between about 1 and 10 residence times in length.

29. A process as claimed in claim 28, wherein each period is between about 6 and 8 residence times in length.

30. A process as claimed in claim 24, wherein inhibition of multiplication of said microorganism is effected by shifting the pH of said culture to a value outside a range tolerated by said microorganism.

31. A process as claimed in claim 30, wherein the pH of said culture falls within about 0.3 and 4 pH units outside said range.

32. A process as claimed in claim 31, wherein the pH of said culture falls about 1 pH unit outside said range.

33. A process as claimed in claim 24, wherein said cultivating step comprises inhibiting multiplication of said microorganism when biomass density per residence time of said culture varies no more than about 20%.

34. A process as claimed in claim 32, wherein biomass density of said culture is determined by monitoring the optical density of said culture.

35. A process as claimed in claim 33, wherein inhibition of multiplication of said microorganism is continued until said optical density is no more than about two-thirds of the steady-state optical density value of said culture.

36. A process as claimed in claim 24, further comprising the step of monitoring concentration of said exoenzyme in said culture.

37. A process as claimed in claim 36, wherein said cultivating step comprises inhibiting multiplication of said microorganism when said monitoring indicates that the concentration of said exoenzyme has declined to a value no more than one-half of a maximum value previously monitored.

38. A process as claimed in claim 37, wherein inhibition of multiplication of said microorganism is continued until said culture has a biomass density that is no more than about two-thirds of the steady-state biomass density of said culture.

39. A process as claimed in claim 24, wherein said exoenzyme-producing microorganism is a bacterium of the genus Bacillus.

40. A process as claimed in claim 24, wherein said fermenter has flow rates ranging from about 0.01 to 2 $h^{-1}$.

41. A process as claimed in claim 24, wherein said fermenter comprises a stirred vessel reactor having a temperature of about 30° to 37° C., aeration at about 0.3 to 3 VVm and a pH between about 6 to 8, said reactor being stirred at up to 1,000 rpm.

* * * * *